US012685457B2

(12) United States Patent
Bollenbeck

(10) Patent No.: US 12,685,457 B2
(45) Date of Patent: Jul. 21, 2026

(54) MAGNETIC RESONANCE APPARATUS WITH A PATIENT DISPLAY UNIT

(71) Applicant: Siemens Healthcare GmbH, Erlangen (DE)

(72) Inventor: Jan Bollenbeck, Eggolsheim (DE)

(73) Assignee: Siemens Healthineers AG, Erlangen (DE)

( * ) Notice: Subject to any disclaimer, the term of this patent is extended or adjusted under 35 U.S.C. 154(b) by 1035 days.

(21) Appl. No.: 17/870,416

(22) Filed: Jul. 21, 2022

(65) Prior Publication Data

US 2023/0022887 A1 Jan. 26, 2023

(30) Foreign Application Priority Data

Jul. 21, 2021 (EP) ..................................... 21187024

(51) Int. Cl.
*A61B 5/055* (2006.01)
*G01R 33/565* (2006.01)
*G01R 33/567* (2006.01)

(52) U.S. Cl.
CPC ........ *A61B 5/055* (2013.01); *G01R 33/56509* (2013.01); *G01R 33/5676* (2013.01)

(58) Field of Classification Search
CPC .......... G01R 33/56509; G01R 33/5676; G01R 33/283; A61B 5/7445; A61B 5/055
See application file for complete search history.

(56) References Cited

U.S. PATENT DOCUMENTS

| | | | | |
|---|---|---|---|---|
| 5,877,732 A * | 3/1999 | Ziarati | ................... | A61B 5/055 |
| | | | | 600/418 |
| 6,198,285 B1 * | 3/2001 | Kormos | ............... | A61B 5/0017 |
| | | | | 324/318 |
| 6,704,592 B1 * | 3/2004 | Reynolds | ............... | A61B 5/055 |
| | | | | 324/322 |
| 8,483,797 B2 * | 7/2013 | Hempel | .................. | A61B 6/032 |
| | | | | 348/817 |
| 8,805,476 B2 * | 8/2014 | Yang | .................... | A61B 5/0033 |
| | | | | 600/418 |
| 10,241,385 B2 | 3/2019 | Hotta et al. | | |
| 2005/0151538 A1 | 7/2005 | Ichinose et al. | | |
| 2005/0273000 A1 * | 12/2005 | Dinehart | .............. | G01R 33/283 |
| | | | | 600/410 |
| 2006/0079763 A1 | 4/2006 | Jeung et al. | | |
| 2007/0247422 A1 * | 10/2007 | Vertegaal | ................ | G06F 3/017 |
| | | | | 345/156 |
| 2013/0162510 A1 * | 6/2013 | Ohgishi | .................. | G09G 3/344 |
| | | | | 324/318 |

(Continued)

FOREIGN PATENT DOCUMENTS

| | | | | | |
|---|---|---|---|---|---|
| CN | 101213467 A | * | 7/2008 | .......... | G01R 33/283 |
| EP | 3581109 A1 | | 12/2019 | | |

(Continued)

OTHER PUBLICATIONS

Kim Do Yoon et al: "Stretchable and Reflective Displays: Materials, Technologies and Strategies"; Nano Convergence, [Online]; vol. 6, No. 1, Jun. 20 2019 (Jun. 20 2019), XP55851163.

(Continued)

*Primary Examiner* — Brian L Casler

(74) *Attorney, Agent, or Firm* — Banner & Witcoff, Ltd.

(57) ABSTRACT

A magnetic resonance apparatus with a scanner unit, a patient receiving area at least partly surrounded by the scanner unit, and a patient display unit arranged within the patient receiving area, wherein the patient display unit includes a reflective display.

6 Claims, 1 Drawing Sheet

(56)  References Cited

U.S. PATENT DOCUMENTS

| | | | | |
|---|---|---|---|---|
| 2015/0297148 A1* | 10/2015 | Biber | .................... | A61B 5/055 |
| | | | | 600/418 |
| 2017/0123021 A1 | 5/2017 | Takamori et al. | | |
| 2017/0322271 A1 | 11/2017 | Gulaka et al. | | |
| 2018/0078217 A1* | 3/2018 | Nufer | .................... | A61B 5/055 |
| 2018/0185113 A1 | 7/2018 | Gregerson et al. | | |
| 2021/0244283 A1 | 8/2021 | Krueger et al. | | |
| 2022/0034984 A1 | 2/2022 | Lamerichs et al. | | |

FOREIGN PATENT DOCUMENTS

| | | | |
|---|---|---|---|
| EP | 3660530 A1 | 6/2020 | |
| JP | 6656881 B2 | 3/2020 | |
| WO | WO-2007004145 A2 * | 1/2007 | .......... G01R 33/283 |
| WO | 2016068420 A1 | 5/2016 | |
| WO | 2018049196 A1 | 3/2018 | |

OTHER PUBLICATIONS

Innovision "Give Patients the Best MRI Experience with Innovision"; https://innoveremedical.com/; Date of screenshot: May 14, 2021.

Philips "MRI In-Bore Experience "; https://www.usa.philips.com/healthcare/education-resources/technologies/mri/mri-in-bore-experience; Status: Jun. 24, 2022.

Wikipedia "Elektronisches Papier"; https://de.wikipedia.org/wiki/Elektronisches_Papier; Date of screenshot: May 14, 2021.

* cited by examiner

MAGNETIC RESONANCE APPARATUS WITH A PATIENT DISPLAY UNIT

TECHNICAL FIELD

The present disclosure relates to a magnetic resonance apparatus with a scanner unit, a patient receiving area at least partly surrounded by the scanner unit, and a patient display unit arranged within the patient receiving area.

BACKGROUND

Magnetic resonance examinations of patients last for a relatively long examination time. During this examination time the patient, in particular the region of the patient to be examined, is located within a patient receiving area of the magnetic resonance apparatus. This being the case, there is frequently a need to communicate information and/or instructions to the patient during the course of the magnetic resonance examination. Due to, in some cases, very loud operating noises of a magnetic resonance apparatus, ear defenders are available to the patient during the magnetic resonance examination. In order, despite this, to make audio communication possible between the patient and the medical operating personnel during the course of the magnetic resonance examination, it is also known for the patient additionally to put on a bulky headset.

However, audio communication for patients who have a reduced hearing capability is additionally made more difficult or is not possible. It is therefore desirable that an optical and/or visual communication path is additionally available for patients. An installation of a standard LED display or an LCD (Liquid Crystal Display) in the area, which can be seen during the examination of the patient, in particular within the patient receiving area, is difficult to arrange however, since these displays are rigid and cannot be adapted to the curvature of a housing surrounding the patient receiving area. Furthermore such displays generate electromagnetic interference, which can potentially lead to image artifacts in the image data acquired. Moreover, such displays have a high power consumption.

In order to make visual information available in the patient receiving area for the patient, it has previously been known for information to be projected on a wall and be projected via a mirror system into the patient receiving area for display for the patient. These types of arrangements with a mirror system take up a great deal of space within the patient receiving area however and thus limit the space and/or room available for the patient.

SUMMARY

An underlying object of the present disclosure is specifically to make available a simple and space-saving integration of a visual communication unit for the patient during a magnetic resonance apparatus.

The disclosure is based on a magnetic resonance apparatus with a scanner unit, a patient receiving area at least partly surrounded by the scanner unit, and a patient display unit arranged within the patient receiving area. In accordance with the disclosure it is proposed that the patient display unit comprises a reflective display.

The magnetic resonance apparatus preferably comprises a medical and/or diagnostic magnetic resonance apparatus, which is designed and/or embodied for acquiring medical and/or diagnostic image data, in particular medical and/or diagnostic magnetic resonance image data, of a patient. To this end the magnetic resonance apparatus comprises the scanner unit. The scanner unit of the magnetic resonance apparatus preferably comprises a detector unit, in particular a magnet unit, for acquiring the medical and/or diagnostic image data. Advantageously here the scanner unit, in particular the magnet unit, comprises a basic magnet, a gradient coil unit and a radio-frequency antenna unit. The radio-frequency antenna unit is permanently arranged within the scanner unit and is designed and/or embodied for emitting an excitation pulse. To acquire the magnetic resonance signals the magnetic resonance apparatus has local radio-frequency coils, which are arranged around the region of the patient to be examined.

The basic magnet of the scanner unit is embodied to create a homogeneous basic magnetic field with a defined and/or specific magnetic field strength, such as for example with a defined and/or specific magnetic field strength of 3 T or 1.5 T etc. In particular the basic magnet is embodied to create a strong, constant and homogeneous basic magnetic field. The homogeneous basic magnetic field is preferably arranged and/or to be found within the patient receiving area of the magnetic resonance apparatus. The gradient coil unit is embodied for creating magnetic field gradients, which are used for spatial encoding during imaging.

The patient receiving area is designed and/or embodied for imaging the patient, in particular the region of the patient, to be examined, for a medical magnetic resonance examination. For this purpose for example the patient receiving area is embodied in the shape of a cylinder and/or is surrounded in a cylindrical shape by the scanner unit. To this end the scanner unit has a housing of the housing unit at least partly surrounding the patient receiving area. The housing surrounding the patient receiving area can also be embodied here as one part and/or in one piece with the side of the radio-frequency antenna unit of the scanner unit facing towards the patient receiving area or can also be embodied separately from the radio-frequency antenna unit of the scanner unit.

A Field of View (FOV) and/or an isocenter of the magnetic resonance apparatus is preferably arranged within the patient receiving area. The FOV preferably comprises an acquisition region of the magnetic resonance apparatus, within which the conditions for an acquisition of medical image data, in particular magnetic resonance image data, are present, such as for example a homogeneous basic magnetic field. The isocenter of the magnetic resonance apparatus preferably comprises the region and/or point within the magnetic resonance apparatus that has the optimal and/or ideal conditions for the acquisition of medical image data, in particular magnetic resonance image data. In particular the isocenter comprises the most homogenous magnetic field region within the magnetic resonance apparatus.

The patient support apparatus is embodied for positioning and/or support of the patient for a magnetic resonance examination. The patient support apparatus in this case may comprise a patient table, which is embodied so that it can be moved into the patient receiving area. For a magnetic resonance examination the patient is positioned on the patient table in such a way that the region to be examined is arranged and/or positioned within the isocenter of the patient receiving area after a positioning of the patient table within the patient receiving area.

For a communication and/or an exchange of information between the patient and the medical operating personnel during a magnetic resonance examination, the magnetic resonance apparatus has a communication unit. The communication unit preferably has a communication element on the user side, such as for example a communication console for input and/or output of communication data, such as information for example. Furthermore the communication unit on the patient side likewise has at least one communication element. In particular the communication unit has a visual communication element, which is embodied as a patient display unit.

The patient display unit preferably has a display surface, in particular a patient display, which is arranged within the patient receiving area. The patient display unit, in particular the patient display, is embodied for a visual and/or optical output of information and/or instructions to the patient during the magnetic resonance examination. The patient display unit, in particular the patient display, has a reflective display in this case. The reflective display preferably comprises a passive display and/or a non-illuminated display of content and/or information on the display and/or a presentation surface. Preferably the reflective display is an E-paper display. Reflective displays and/or E-paper displays reflect light like normal paper. Frequently in such cases reflective displays and/or E-paper displays are constructed in such a way that a distance of imaging elements from the surface, in particular an output surface and/or a presentation surface, is less than with conventional displays, such as for example an LC display.

The disclosure has the advantage that a displayed image content, due to a short distance between the imaging elements and the display surface and/or or presentation surface, looks the same from all viewing angles onto the display surface and/or presentation surface. Moreover, by means of reflective displays and/or E-paper displays, static displays over a longer period are realized in an especially energy-saving way, since with these displays, a current flow is only required for a change to the image content, for example a page change. The static display can moreover be operated without flicker. A further advantage is that a display on the reflective display and/or the E-paper display is easily able to be read and/or recognized by a patient both in a dark environment and also in a bright environment. Moreover reflective displays and/or E-paper displays are embodied very thin and light, so that a space-saving arrangement can be achieved within the patient receiving area and room and/or space available for the patient within the patient receiving area is essentially hardly restricted at all.

In an advantageous development of the disclosed magnetic resonance apparatus there can be provision for the patient receiving area to have a housing surrounding the patient receiving area with an inner wall and for the reflective display to be arranged on the inner wall surrounding the patient receiving area to the top. Preferably the reflective display and/or the E-paper display is arranged on an inner wall of the housing surrounding the patient receiving area opposite to a support area, which is designed and/or embodied for supporting a patient's head. This enables an advantageous visibility of the reflective display and/or of the E-paper display to be achieved for a patient during a magnetic resonance examination and/or while the patient is in the patient receiving area.

In an advantageous development of the disclosed magnetic resonance apparatus, the reflective display has a shape adapted to a surface shape of the inner wall of the housing surrounding the patient receiving area. Preferably here the reflective display and/or the E-paper display is embodied flexibly and can thereby be adapted especially easily to the shape of the surface of the inner wall of the housing surrounding the patient receiving area. In this way an especially space-saving arrangement of the patient display unit, in particular of the reflective display and/or of the E-paper display, within the patient receiving area is achieved. In particular in this way a precise-fit arrangement of the reflective display and/or of the E-paper display on the surface shape of the inner wall can be achieved.

In an advantageous development of the disclosed magnetic resonance apparatus, there can be provision for the magnetic resonance apparatus to have a data transmission unit, which is embodied for data transmission to the reflective display. The data transmission unit in this case can comprise a wired data transmission and/or a data transmission by means of optical fibers and/or a data transmission by means of a standard radio protocol, such as for example by means of Bluetooth, and/or a data transmission by means of optical data transmission techniques, such as for example by means of infrared data transmission. Moreover, further transmission techniques appearing sensible to the person skilled in the art are always possible.

In an advantageous development of the disclosed magnetic resonance apparatus, the magnetic resonance apparatus has a display control unit, wherein by means of the display control unit a data transmission to the reflective display and/or a signal processing by the reflective display is deactivated during an acquisition of magnetic resonance data.

The display control unit comprises at least one processing module and/or a processor, wherein the display control unit is embodied for controlling the patient display unit, in particular the reflective display and/or the E-paper display. Thus in particular the display control unit is embodied, for control of the patient display unit, in particular of the reflective display and/or the E-paper display, to carry out computer-readable instructions. In particular the display control unit comprises a memory unit, wherein computer-readable information is stored on the memory unit, wherein the display control unit is embodied to load the computer-readable information from the memory unit and to carry out the computer-readable information. The components of the display control unit can predominantly be embodied in the form of software components. Basically however these components can also be realized in part, in particular when it is a matter of especially fast computations, in the form of software-supported hardware components, for example FPGAs or the like. Likewise the interfaces needed, for example if it is only a matter of accepting data from other software components, can be embodied as software interfaces. They can however also be embodied as interfaces constructed from hardware, which are controlled by suitable software. Naturally it is also conceivable for a number of the said components to be realized grouped together in the form of an individual software component or software-supported hardware component.

The acquisition of magnetic resonance data is preferably done in magnetic resonance data acquisition time windows. During these magnetic resonance data acquisition time windows the data transmission to the reflective display and/or a signal processing by the reflective display is prevented and/or deactivated. This aspect of the disclosure has the advantage that an unwanted disruption of a magnetic resonance data acquisition is advantageously prevented and thus image artifacts in the acquired magnetic resonance image data can also be prevented.

In an advantageous development of the disclosed magnetic resonance apparatus there can be provision, during the acquisition of magnetic resonance data, for a static presentation of image information and/or instructions to be shown by the reflective display. Due to the static and/or permanent display of image information and/or instructions during the acquisition of magnetic resonance data, in particular during the magnetic resonance data acquisition time window, the patient can continue to receive information. This static and/or permanent display during the magnetic resonance data acquisition time window can contribute to keeping the patient calm and, in this way, also contribute to a high quality of the acquired image data.

BRIEF DESCRIPTION OF THE DRAWING

Further advantages, features and details of the disclosure emerge from the exemplary aspect described below and also with the aid of the drawings.

In the figures.

DETAILED DESCRIPTION

Figure 1:
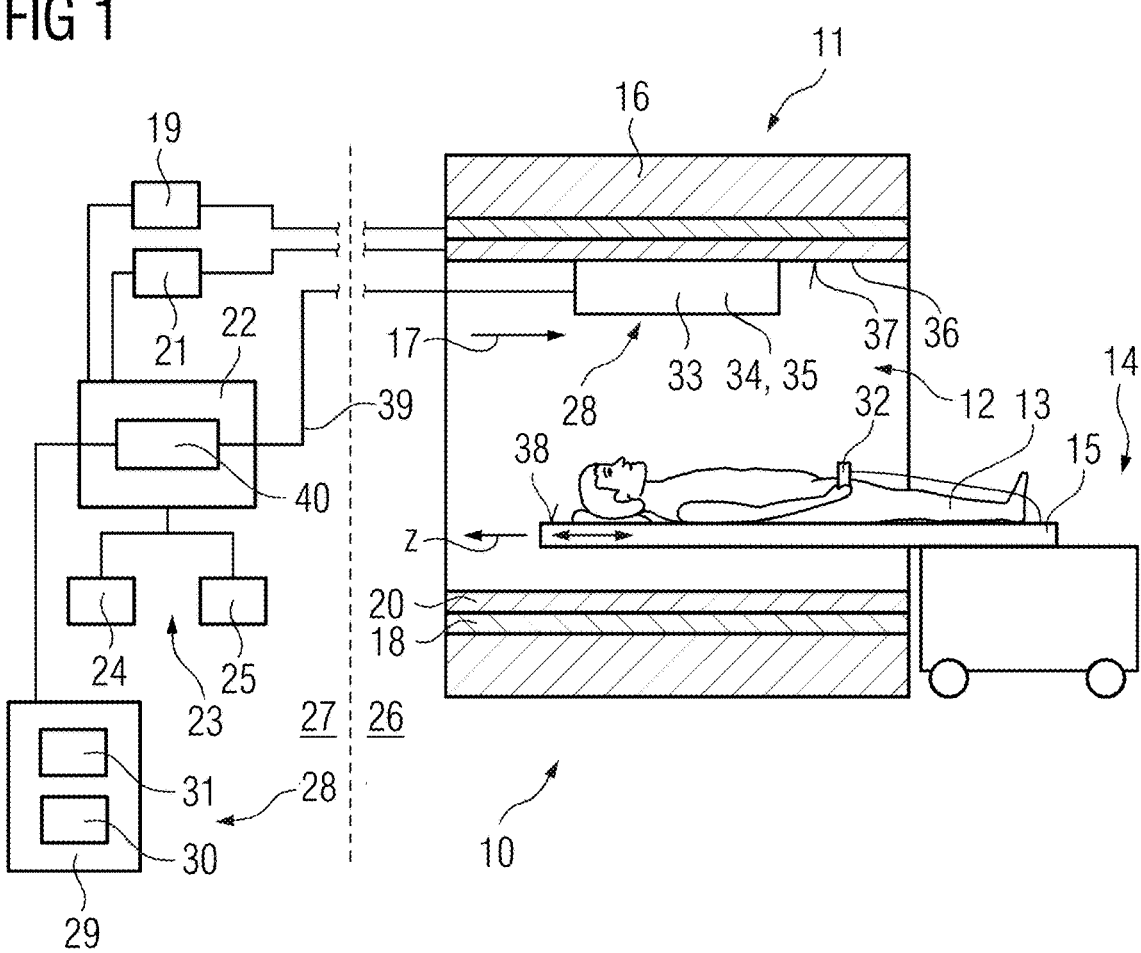
FIG. 1 shows a magnetic resonance apparatus with a patient display unit in a schematic diagram.

Shown schematically in FIG. 1 is a magnetic resonance apparatus 10. The magnetic resonance apparatus 10 comprises a scanner unit 11 formed by a magnet unit. Moreover the magnetic resonance apparatus 10 has a patient receiving area 12 for imaging a patient 13. The patient receiving area 12 in the present exemplary aspect is embodied cylindrical in shape and is surrounded in a cylindrical shape in a circumferential direction by the scanner unit 11, in particular by the magnet unit. Basically however an aspect of the patient receiving area 12 that differs from this is always conceivable. The patient 13 can be pushed and/or moved by means of a patient support apparatus 14 of the magnetic resonance apparatus 10 into the patient receiving area 12. To this end the patient support apparatus 14 has a patient table 15 embodied for movement within the patient receiving area 12. Here in particular the patient table 15 is supported for movement in the direction of a longitudinal extent of the patient receiving area 12 and/or in the z direction.

The scanner unit 11, in particular the magnet unit, comprises a superconducting basic magnet 16 for creating a strong and in particular constant basic magnetic field 17. Furthermore the scanner unit 11, in particular the magnet unit, has a gradient coil unit 18 for creating magnetic field gradients, which are used for spatial encoding during imaging. The gradient coil unit 18 is controlled by means of a gradient control unit 19 of the magnetic resonance apparatus 10. The scanner unit 11, in particular the magnet unit, furthermore comprises a radio-frequency antenna unit 20 for exciting a polarization, which is set in the basic magnetic field 17 created by the basic magnet 16. The radio-frequency antenna unit 20 is controlled by a radio-frequency antenna control unit 21 of the magnetic resonance apparatus 10 and radiates radio-frequency magnetic resonance sequences into the patient receiving area 12 of the magnetic resonance apparatus 10.

For control of the basic magnet 16, of the gradient control unit 19 and for control of the radio-frequency antenna control unit 21, the magnetic resonance apparatus 10 has a system control unit 22. The system control unit 22 centrally controls the magnetic resonance apparatus, such as for example the carrying out of a prespecified imaging gradient echo sequence. Moreover the system control unit 22 comprises an evaluation unit, not shown in any greater detail, for evaluation of medical image data that is acquired during the magnetic resonance examination.

Furthermore the magnetic resonance apparatus 10 comprises a user interface 23, which is connected to the system control unit 22. Control information such as for example imaging parameters, as well as reconstructed magnetic resonance images, can be displayed on a display unit 24, for example on at least one monitor, of the user interface 23 for a medical operator. Furthermore the user interface 23 has an input unit 25, by means of which information and/or parameters can be entered during a measurement process by the medical operating personnel.

The scanner unit 11 of the magnetic resonance apparatus 10 is arranged together with the patient support apparatus 14 within an examination room 26. The system control unit 22 on the other hand is arranged, together with the user interface 23, within a control room 27. The control room 27 is embodied separated from the examination room 26. In particular the examination room 26 is screened from the control room 27 in respect of radio-frequency radiation. During a magnetic resonance examination, the patient 13 is located within the examination room 26, on the other hand the medical operating personnel are mostly within the control room 27.

For a communication and/or an exchange of information between the patient 13 and the medical operating personnel during a magnetic resonance examination, the magnetic resonance apparatus 10 has a communication unit 28 (FIG. 1). On the operator side the communication unit 28 has a communication element embodied as an operator console 29. The communication element, in particular the operator console 28, is preferably arranged within the control room 27. The operator console 29 has an input element 30 and an output element 31. The input element 30 and/or the output element 31 can be embodied in this case as an acoustic and/or visual input element 30 and/or output element 31.

Furthermore the communication unit 28 on the patient side has a first communication element, which is embodied as an input element 32. By means of the input element 32 the patient 13 can inform the operator, in particular the medical operating personnel, about a feeling, such as for example of not feeling well, during the magnetic resonance examination. In the present exemplary aspect the input element 32 is embodied as a patient call ball. Basically however further input elements 32 appearing sensible to the person skilled in the art, such as for example a microphone etc. are possible in a further aspect of the communication unit 28. The communication unit 28 furthermore has a second communication element on the patient side, which is embodied as output element 33. The output element 33 is embodied as a patient display unit 34. The patient display unit 34 comprises a reflective display 35, which is embodied as an E-paper display.

The patient display unit 34, in particular the reflective display 35 and/or the E-paper display, is arranged within the patient receiving area 12. The patient receiving area 12 comprises a housing 36 surrounding the patient receiving area 12 with an inner wall 37. The housing 36 surrounding the patient receiving area 12 in the present exemplary aspect is embodied as a single part with the radio-frequency antenna unit 20, in particular a side of the radio-frequency antenna unit 20 facing towards the patient receiving area 12. In an alternate aspect of the disclosure the housing 36 surrounding the patient receiving area 12 can also form a separate unit from the radio-frequency antenna unit 20.

The reflective display 35 and/or the E-paper display is arranged on the inner wall 37 of the housing 36 surrounding the patient receiving area 12 surrounding the patient receiving area 12 above. In this way the reflective display 35 and/or the E-paper display is arranged on one side of the patient receiving area 12, which is arranged opposite a support surface 38 for supporting the patient 13, in particular the head of the patient 13.

Figure 2:
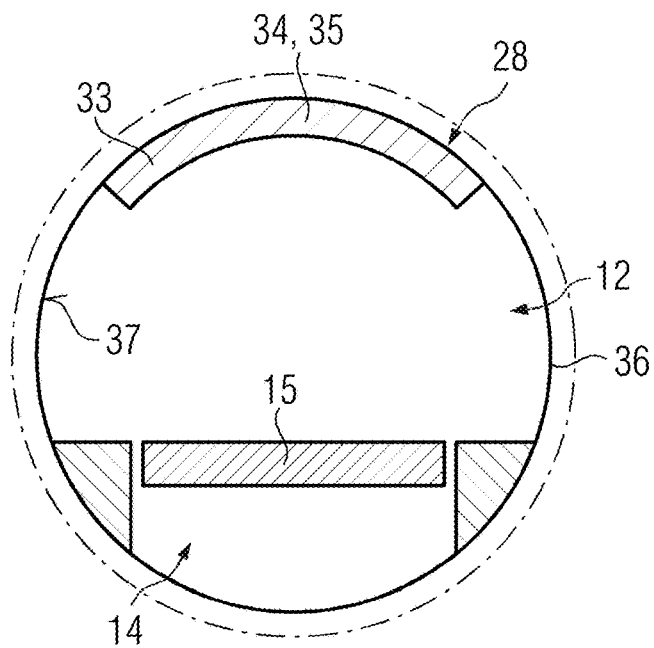
FIG. 2 shows a cross section through the patient receiving area with the patient display unit.

The reflective display 35 and/or the E-Paper display is embodied especially thin and flexible. In this case the reflective display 35 and/or the E-paper display has a shape that is adapted to a surface shape of the inner wall 37 of the housing 36 surrounding the patient receiving area 12. Here in particular the reflective display 35 and/or the E-paper display is arranged to fit precisely adapted to the shape of the surface of the inner wall 37, as can be seen in FIG. 2, a cross-section through the patient receiving area 12.

The magnetic resonance apparatus 10, in particular the communication unit 28, furthermore has a data transmission unit 39, wherein the data transmission unit 39 is embodied for a data transmission of communication data, in particular visual communication data, to the reflective display 35 and/or the E-paper display (FIG. 1). The data transmission unit 39 in this case can comprise means for a wired data transmission and/or for a data transmission by means of optical waveguides and/or a data transmission by means of a standard radio protocol, such as for example by means of Bluetooth, and/or optical data transmission techniques, such as for example by means of infrared data transmission. Moreover, further transmission techniques appearing sensible to the person skilled in the art are always possible.

The magnetic resonance apparatus 10, in particular the communication unit 28, furthermore has a display control unit 40. In the present exemplary aspect the display control unit 40 is integrated within the system control unit 22. In an alternate aspect of the display control unit 40 said unit can also be embodied separately from the system control unit 22.

A communication via the reflective display 35 and/or the E-paper display is controlled by means of the display control unit 40. In this case the display control unit 40 is embodied for a data transmission to the reflective display 35 and/or a signal processing by the reflective display 35 during an acquisition of magnetic resonance data to be deactivated by means of the display control unit 40. The acquisition of magnetic resonance data is preferably done in magnetic resonance data acquisition time windows. During these magnetic resonance data acquisition time windows the data transmission to the reflective display 35 and/or a signal processing by the reflective display 35 is prevented and/or deactivated by means of the display control unit 40. Moreover, during the acquisition of magnetic resonance data, in particular in these magnetic resonance data acquisition time windows, static and/or permanent image information is displayed for the patient 13 by means of the reflective display 35 and/or the E-paper display.

The magnetic resonance apparatus 10 shown can of course comprise further components that magnetic resonance apparatuses 10 usually have. The general way in which a magnetic resonance apparatus 10 functions is moreover known to the person skilled in the art, so that a further detailed description of the further components are not provided here.

Although the disclosure has been illustrated and described in greater detail by the preferred exemplary aspect, the disclosure is not restricted by the disclosed examples and other variations can be derived herefrom by the person skilled in the art, without departing from the scope of protection of the disclosure.

The invention claimed is:

1. A magnetic resonance apparatus comprising:
a scanner unit;
a patient receiving area at least partly surrounded by the scanner unit;
a patient display unit arranged within the patient receiving area, wherein the patient display unit comprises a reflective display; and
a display control unit, integrated within a system control unit of the magnetic resonance apparatus,
wherein the display control unit is configured to prevent and/or deactivate data transmission to the reflective display and/or a signal processing by the reflective display during magnetic resonance data acquisition time windows.

2. The magnetic resonance apparatus as claimed in claim 1, wherein the reflective display comprises an E-paper display.

3. The magnetic resonance apparatus as claimed in claim 1, wherein the patient receiving area has a housing surrounding the patient receiving area with an inner wall, and the reflective display is arranged on the inner wall surrounding the patient receiving area above the patient receiving area.

4. The magnetic resonance apparatus as claimed in claim 3, wherein the reflective display has a shape adapted to a surface shape of the inner wall of the housing surrounding the patient receiving area.

5. The magnetic resonance apparatus as claimed in claim 1, wherein a data transmission unit is embodied for a data transmission to the reflective display.

6. The magnetic resonance apparatus as claimed in claim 1, wherein a static display of image information by the reflective display is showable during the acquisition of magnetic resonance data.

* * * * *